(12) United States Patent
Austin et al.

(10) Patent No.: US 7,815,670 B2
(45) Date of Patent: Oct. 19, 2010

(54) METHOD OF LOADING A MEDICAL ENDOPROSTHESIS THROUGH THE SIDE WALL OF AN ELONGATE MEMBER

(75) Inventors: Michael Austin, Newport (IE); Aiden Flanagan, Galway (IE); Dave McMorrow, Galway (IE); Gabriel Sobrino Serrano, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1103 days.

(21) Appl. No.: 11/484,528

(22) Filed: Jul. 11, 2006

(65) Prior Publication Data

US 2008/0015674 A1  Jan. 17, 2008

(51) Int. Cl.
*A61F 2/06* (2006.01)
(52) U.S. Cl. ..................................... 623/1.11
(58) Field of Classification Search ............ 623/1.11
See application file for complete search history.

(56) References Cited

U.S. PATENT DOCUMENTS

| 4,580,568 | A | 4/1986 | Gianturco |
| 4,655,771 | A | 4/1987 | Wallsten |
| 4,681,110 | A | 7/1987 | Wiktor |
| 4,768,507 | A | 9/1988 | Fischell et al. |
| 4,950,227 | A | 8/1990 | Savin et al. |
| 5,026,377 | A | 6/1991 | Burton et al. |
| 5,201,757 | A | 4/1993 | Heyn et al. |
| 5,683,451 | A | * | 11/1997 | Lenker et al. ............ 623/1.11 |
| 5,709,703 | A | * | 1/1998 | Lukic et al. ............. 623/1.12 |
| 5,749,921 | A |  | 5/1998 | Lenker et al. |
| 5,824,041 | A |  | 10/1998 | Lenker et al. |
| 5,968,068 | A |  | 10/1999 | Dehdashtian et al. |
| 6,110,191 | A |  | 8/2000 | Dehdashtian et al. |
| 6,141,855 | A |  | 11/2000 | Morales |
| 6,319,275 | B1 |  | 11/2001 | Lashinski et al. |
| 6,322,586 | B1 |  | 11/2001 | Monroe et al. |
| 6,471,718 | B1 |  | 10/2002 | Staehle et al. |
| 6,723,071 | B2 | * | 4/2004 | Gerdts et al. ............ 604/103.04 |
| 6,858,034 | B1 |  | 2/2005 | Hijlkema et al. |
| 2003/0083730 | A1 |  | 5/2003 | Stinson |
| 2003/0139795 | A1 |  | 7/2003 | Olson |
| 2004/0215070 | A1 | * | 10/2004 | Letort et al. ............. 600/364 |
| 2004/0249433 | A1 |  | 12/2004 | Freitag |
| 2004/0260379 | A1 |  | 12/2004 | Jagger et al. |
| 2005/0166389 | A1 |  | 8/2005 | Perreault et al. |
| 2006/0064152 | A1 |  | 3/2006 | Olson |
| 2006/0100689 | A1 | * | 5/2006 | Pryor ..................... 623/1.12 |
| 2006/0184226 | A1 |  | 8/2006 | Austin |

FOREIGN PATENT DOCUMENTS

| EP | 1656908 | 5/2006 |
| SU | 1768068 | 10/1992 |

OTHER PUBLICATIONS

International Search Report and Written Opinion; PCT/US2007/072474; mailed Dec. 6, 2007.

* cited by examiner

*Primary Examiner*—Todd E Manahan
*Assistant Examiner*—Naquan Ishman
(74) *Attorney, Agent, or Firm*—Crompton, Seager & Tufte, LLC

(57) ABSTRACT

Medical devices and related systems and methods.

12 Claims, 14 Drawing Sheets

METHOD OF LOADING A MEDICAL ENDOPROSTHESIS THROUGH THE SIDE WALL OF AN ELONGATE MEMBER

TECHNICAL FIELD

This disclosure relates to medical devices and related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the outer member to allow the stent to engage the occlusion/lumen wall. Thereafter, the operator removes the distal portion of the system from the lumen.

SUMMARY

Methods of loading an implantable medical endoprosthesis (e.g., a stent) into a medical device include passing the implantable medical endoprosthesis through an aperture (e.g., a slit) formed through a sidewall of an elongate member (e.g., an elongate tubular member) of the medical device. In certain embodiments, the method further includes passing the implantable medical endoprosthesis through an aperture (e.g., a slit) formed through a sidewall of an inner sleeve disposed within a lumen of the elongate member. The apertures of the elongate member and the inner sleeve can, for example, be substantially aligned (e.g., axially and/or circumferentially aligned) with one another and can be configured to allow the implantable medical endoprosthesis to be passed therethrough. The apertures of the elongate member and the inner sleeve can, for example, be about ten percent to about 50 percent and/or about two millimeters to about 20 millimeters longer than the implantable medical endoprosthesis. The apertures can be expanded to have lengths and widths greater than the length and width (e.g., diameter), respectively, of the implantable medical endoprosthesis. After passing the implantable medical endoprosthesis through the apertures of the elongate member and inner sleeve, the implantable medical endoprosthesis becomes disposed within a central lumen of the inner sleeve. The inner sleeve can then be displaced (e.g., proximally displaced) relative to the outer member to transport the implantable medical endoprosthesis away from the region of the elongate member including the aperture (e.g., the slit region of the elongate member). The region of the elongate member including the aperture can then be removed (e.g., cut off), repaired (e.g., bonded closed), and/or reinforced (e.g., disposed within an outer sleeve).

In certain embodiments, methods of loading the implantable medical endoprosthesis (e.g., a stent) into the elongate member include radially compressing the implantable medical endoprosthesis by applying a force to multiple circumferentially spaced tails of a sleeve that at least partially surround the implantable medical endoprosthesis. The sleeve is at least partially disposed within the lumen of the elongate member. After radially compressing the implantable medical endoprosthesis, the elongate member is axially displaced relative to the sleeve and the implantable medical endoprosthesis. In certain embodiments, the tails of the sleeve extend distally beyond the implantable medical endoprosthesis when the implantable medical endoprosthesis is disposed within the sleeve. In such embodiments, while compressing the implantable medical endoprosthesis, distal end portions of the tails can be held in an axially fixed position and tension can be applied to the sleeve (e.g., by pulling proximally on a proximal portion of the sleeve). The sleeve and the implantable medical endoprosthesis can be loaded into the lumen of the elongate member by distally advancing the elongate member over the sleeve and implantable medical endoprosthesis while maintaining the sleeve and implantable medical endoprosthesis in a substantially axially fixed position.

Embodiments may include one or more of the following advantages.

In some embodiments, the implantable medical endoprosthesis is passed through the aperture formed in the side wall of the elongate member. By passing the implantable medical endoprosthesis through the aperture, frictional contact between the outer surface of the implantable medical endoprosthesis and the inner surface of the elongate member can be reduced. For example, axial movement of the implantable medical endoprosthesis relative to the elongate member can be reduced, and thus friction associated with such movement can be reduced. As a result of the reduced friction, scratching or scuffing of the outer surface of the implantable medical endoprosthesis (e.g., to a coating adhered to the outer surface of the implantable medical endoprosthesis) can be reduced (e.g., prevented).

In certain embodiments, the implantable medical endoprosthesis is disposed within the inner sleeve, which is at least partially disposed within the elongate member. While loading the implantable medical endoprosthesis into the elongate member, the implantable medical endoprosthesis and the inner sleeve can be displaced relative to the elongate member. The presence of the inner sleeve between the implantable medical endoprosthesis and the elongate member can reduce (e.g., prevent) friction between the outer surface of the implantable medical endoprosthesis and the elongate member as the inner sleeve and implantable medical endoprosthesis are axially displaced within the elongate member, and can thus help to prevent scratching or scuffing of the outer surface of the stent.

In some embodiments, the implantable medical endoprosthesis is disposed within a region of the sleeve including multiple, circumferentially spaced tails. The implantable medical endoprosthesis can be compressed with the tails of the sleeve at least partially surrounding the implantable medical endoprosthesis. The sleeve and implantable medical endoprosthesis can then be displaced axially into a lumen of the outer member. The tails of the sleeve can help to prevent scratching or scuffing of the outer surface of the implantable medical endoprosthesis as the implantable medical endoprosthesis is compressed and transported into the outer member.

In certain embodiments, end portions of the tails extend beyond an end of the implantable medical endoprosthesis when the implantable medical endoprosthesis is disposed in the sleeve. While the implantable medical endoprosthesis is being compressed, the end portions of the tails can be axially fixed and an axial force can be applied to the sleeve, causing tension within the sleeve. This tension can help to maintain a desired circumferential orientation of the tails while the implantable medical endoprosthesis is being compressed and/or while the outer member is being displaced relative to the sleeve and implantable medical endoprosthesis.

Other aspects and features will be apparent from the description, drawings, and claims.

DESCRIPTION OF DRAWINGS

Like reference symbols in the various drawings indicate like elements.

DETAILED DESCRIPTION

Figure 1:
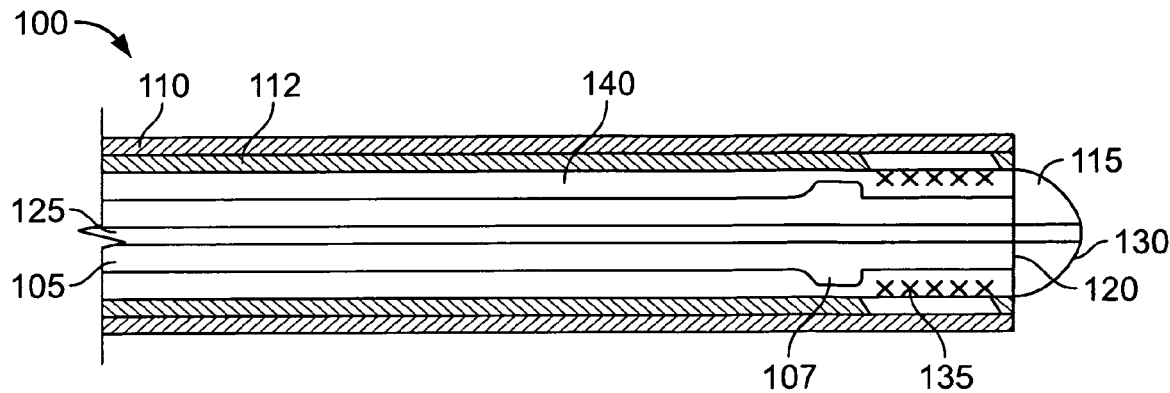
FIG. 1 is a cross-sectional view of a distal portion of an embodiment of a stent delivery system.

Referring to FIG. 1, a stent delivery system 100 includes an inner member 105 disposed within an outer member 110 and an inner sleeve 112. Inner sleeve 112 is disposed within outer member 110 such that the outer surface of inner sleeve 112 is in contact with the inner surface of outer member 110. In some embodiments, the outer surface of inner sleeve 112 is attached (e.g., thermally bonded and/or adhesively bonded) to the inner surface of outer member 110. A flexible tip 115 is attached to a distal end 120 of inner member 105, and a bumper 107 extends circumferentially about inner member 105. A guidewire lumen 125 extends axially through inner member 105 and tip 115, from a proximal end (not shown) of inner member 105 to a distal end 130 of tip 115. A self-expanding stent 135 is contained within the distal region of an annular lumen 140 extending along the length of system 100 between inner sleeve 112 and inner member 105.

Figure 2A:
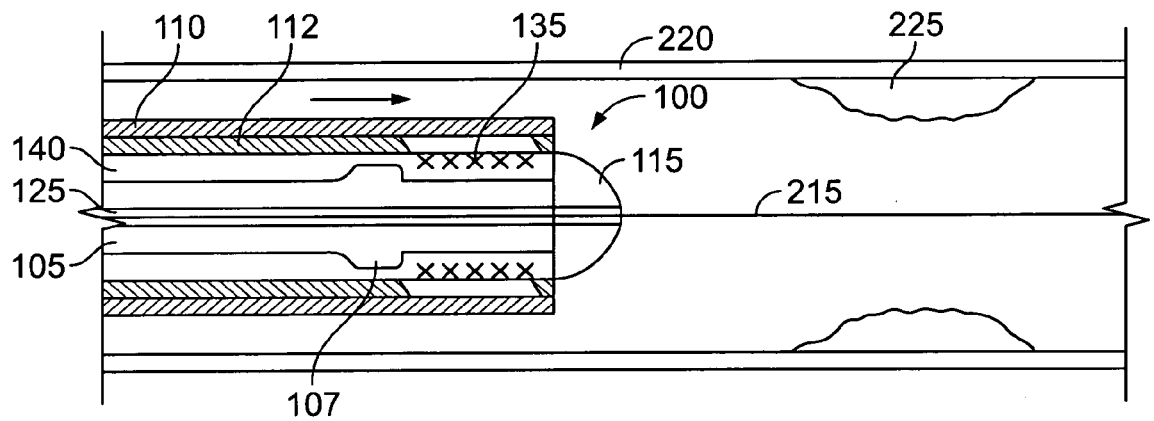
FIGS. 2A-2D illustrate an embodiment of a method and apparatus for loading a stent into an inner sleeve and outer tubular member of a stent delivery system.
Figure 2B:
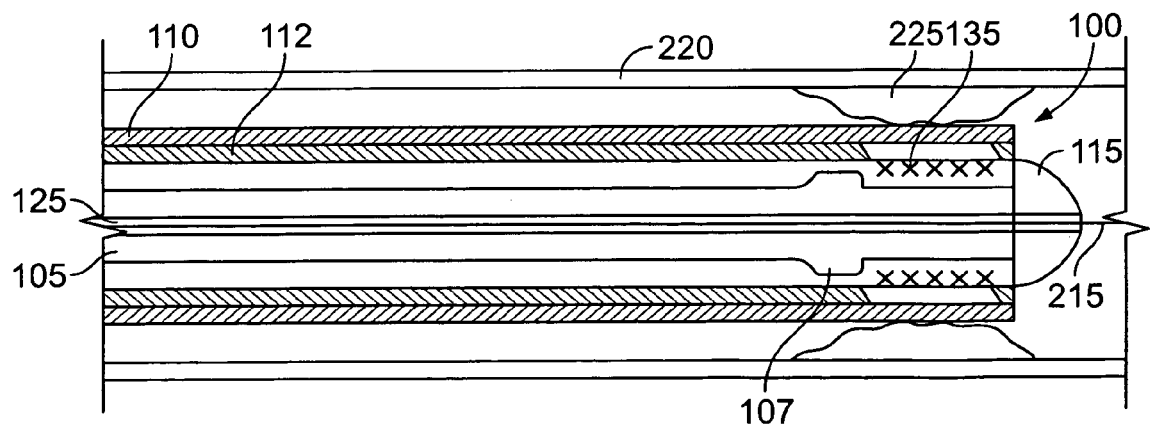
Figure 2C:
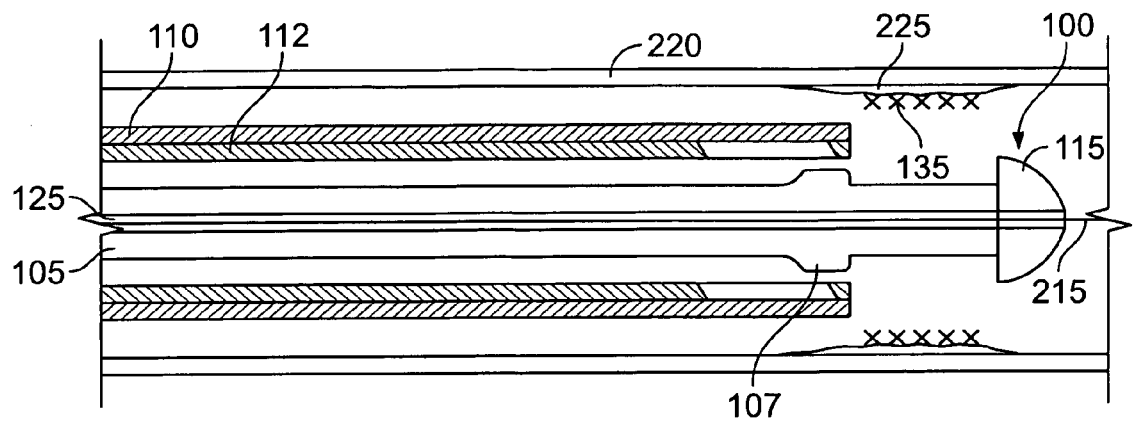
Figure 2D:
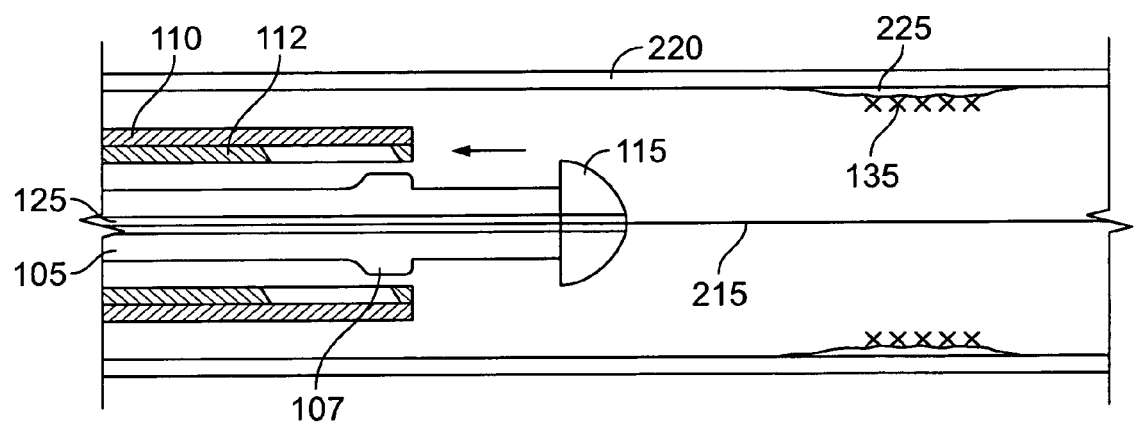

FIGS. 2A-2D illustrate an embodiment of a method of using stent delivery system 100. Referring to FIG. 2A, the method includes inserting a guide wire 215 into a body vessel (e.g., a blood vessel) 220 and then passing stent delivery system 100 over guide wire 215 so that guide wire 215 becomes disposed within guide wire lumen 125 of inner member 105. Stent Delivery system 100 is then advanced along guide wire 215 and through body vessel 220 until the portion of stent delivery system 100 containing stent 135 is positioned within an occluded region 225 of vessel 220, as shown in FIG. 2B. Outer member 110 and inner sleeve 112 are then retracted relative to inner member 105 to deploy stent 135 within vessel 220, as shown in FIG. 2C. As outer member 110 and inner sleeve 112 are retracted, proximal movement of stent 135 is prevented by bumper 107. After stent 135 has been fully deployed, stent delivery system 100 is withdrawn from vessel 220, as shown in FIG. 2D, leaving stent 135 disposed within vessel 220.

Figure 3A:
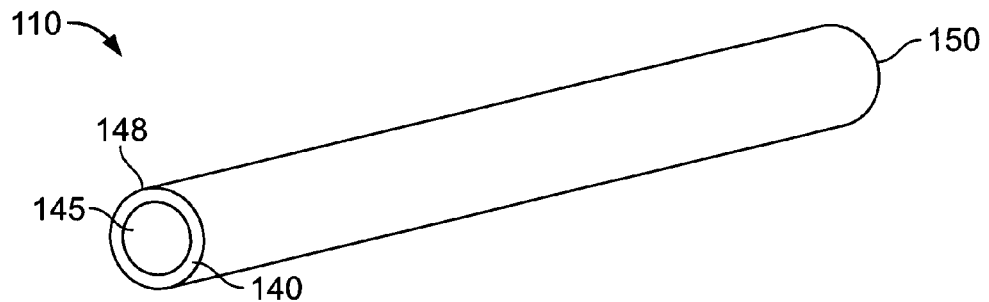
FIGS. 3A-3K illustrate an embodiment of a method of using a stent delivery system.

FIGS. 3A-3K illustrate an embodiment of a method of loading stent 135 into inner sleeve 112 and outer member 110 of stent delivery system 100. Referring to FIG. 3A, outer member 110 includes a side wall 140, and a lumen 145 extends from a proximal end 148 of outer member 110 to a distal end 150 of outer member 110. Outer member 110 is a generally cylindrical tube and can have inner and outer diameters that make outer member 110 suitable for use in a stent delivery system. In some embodiments, outer member 110 has an inner diameter of about one millimeter to about 12 millimeters and/or an outer diameter of about 1.5 millimeters to about 14 millimeters.

Figure 3B:
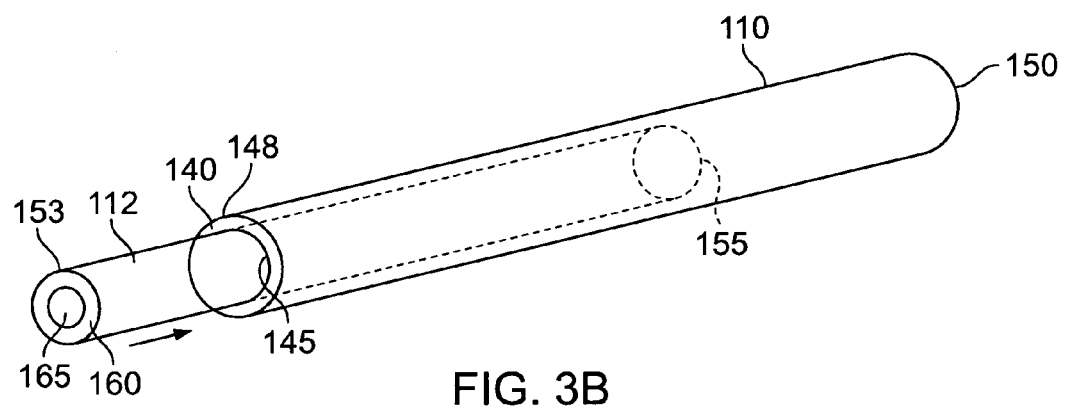

Referring to FIG. 3B, inner sleeve 112 is slid into lumen 145 of outer member 110 via an opening at proximal end 148 of outer member 110. Inner sleeve 112 can, for example, be slid into outer member 110 until a distal end 155 of inner sleeve 112 is substantially aligned with distal end 150 of outer member 110, as shown in FIG. 3C.

Referring again to FIG. 3B, inner sleeve 112 includes a side wall 160, and a lumen 165 extends from a proximal end 153 of inner sleeve 112 to distal end 155 of inner sleeve 112. Inner sleeve 112 is a substantially cylindrical tubular member and has an outer diameter that is slightly less than the inner diameter of outer member 110. The outer diameter of inner sleeve 112 can, for example, be about 0.1 millimeter to about one millimeter less than the inner diameter of outer member 110. In certain embodiments, inner sleeve 112 has an outer diameter of about 1.5 millimeters to about 12 millimeters and/or an inner diameter of about one millimeter to about 11 millimeters.

Figure 3C:
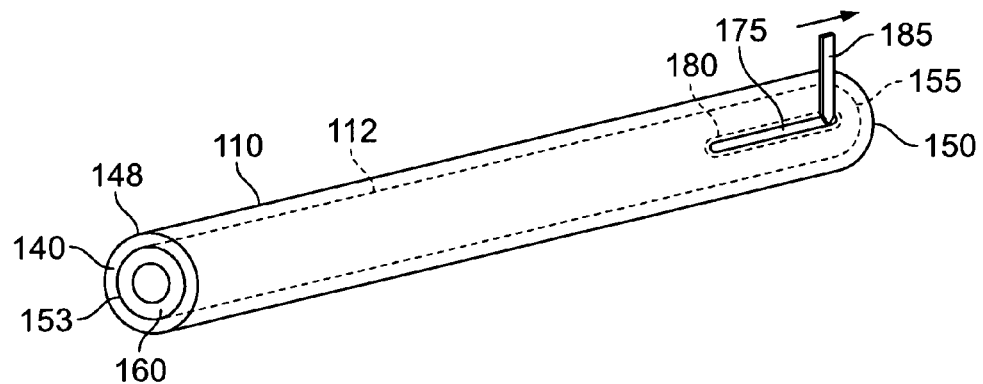
Figure 3D:
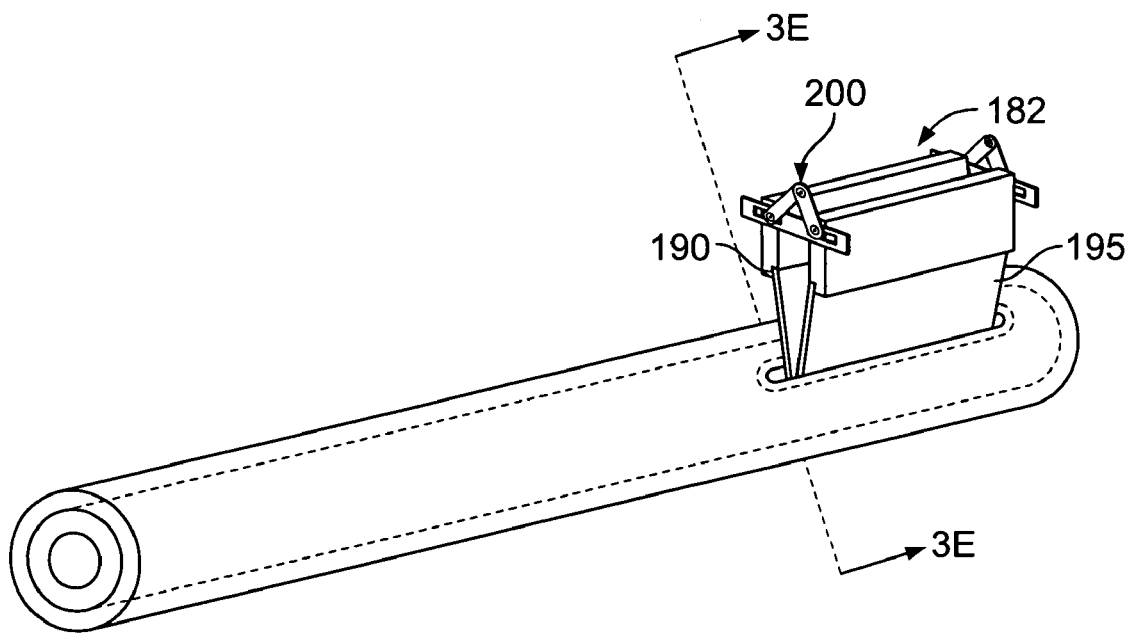

As shown in FIG. 3C, while inner sleeve 112 is disposed within outer member 110, slits 175, 180 are formed in respective side walls 140, 160 of outer member 110 and inner sleeve 112 by puncturing side walls 140, 160 with a sharp blade 185 and moving blade 185 along a predetermined length of outer member 110 and inner sleeve 112. In some embodiments, a mandrel (not shown) is inserted into lumen 165 of inner sleeve 112 prior to puncturing side walls 140, 160. The mandrel can help to provide support to outer member 110 and inner sleeve 112 during the cutting procedure. Slits 175, 180 generally extend substantially parallel to the longitudinal axes of outer member 110 and inner sleeve 112. However, slits 175, 180 can alternatively or additionally extend at an angle (e.g., an acute angle) relative to the longitudinal axes of outer member 110 and inner sleeve 112.

The predetermined length of slits 175, 180, can be a function of the size (e.g., the length and/or diameter) of a stent that is to be passed through slits 175, 180. In some embodiments, for example, slits 175, 180 have respective lengths that are at least about five percent (e.g., at least about 15 percent, about 30 percent to about 45 percent, about 60 percent) greater than the length of the stent to be passed therethrough. In certain embodiments, slits 175, 180 are at least about 0.5 millimeter (e.g., about 0.5 to about 30 millimeters, about 20 millimeters to about 30 millimeters) longer than the stent to be passed therethrough. Providing slits that are longer than the length of the stent can help to ensure that the slits are expandable to a sufficient size (e.g., to a sufficient length and/or width) to allow the stent to be passed therethrough during the stent loading process.

As an alternative to axially moving blade 185 along outer member 110 and inner sleeve 112 to create slits 175, 180, an elongate blade having a length substantially equal to the desired length of slits 175, 180 can be used to puncture side walls 140, 160 of outer member 110 and inner sleeve 112 without substantially axially moving the blade. Moreover, while slits 175, 180 have been described as being formed with a sharp blade, other tools that are capable of penetrating side walls 140, 160 of outer member 110 and inner sleeve 112 can alternatively or additionally be used to form slits 175, 180. Examples of such tools include lasers, die cutters, injection molding devices, chemical etchers, and grinding devices.

Referring to FIGS. 3D-3G, after forming slits 175, 180, an expandable member (e.g., a fixture) 182 is inserted into slits 175, 180 and expanded to expand slits 175, 180. When slits 175, 180 are expanded (as shown, for example, in FIGS. 3F and 3G) the widths of slits 175, 180 increase and their lengths decrease. The widths of slits 175, 180 when expanded can, for example, be at least about one millimeter (e.g., about one millimeter to about ten millimeters, about three millimeters) greater than the unexpanded width or diameter of a stent to be passed through the slits (e.g., the diameter of a compressed stent to be passed through the slits). The lengths of slits 175, 180 when expanded can be at least about one millimeter (e.g., about one to about 20 millimeters, about five millimeters) greater than the length of a stent to be passed through the slits.

Figure 3E:
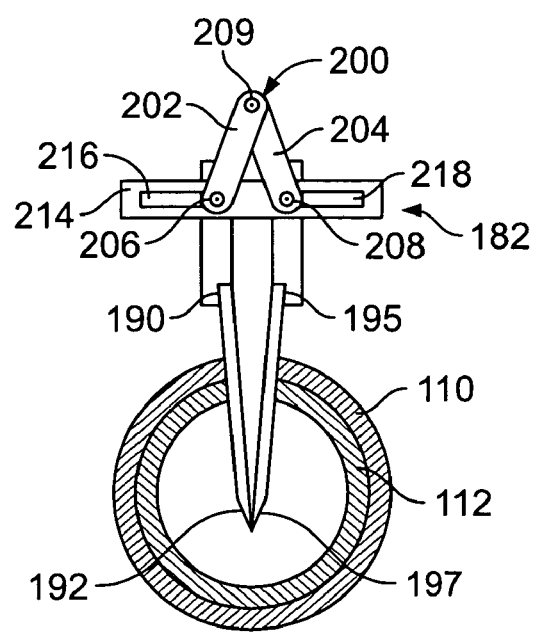
Figure 3F:
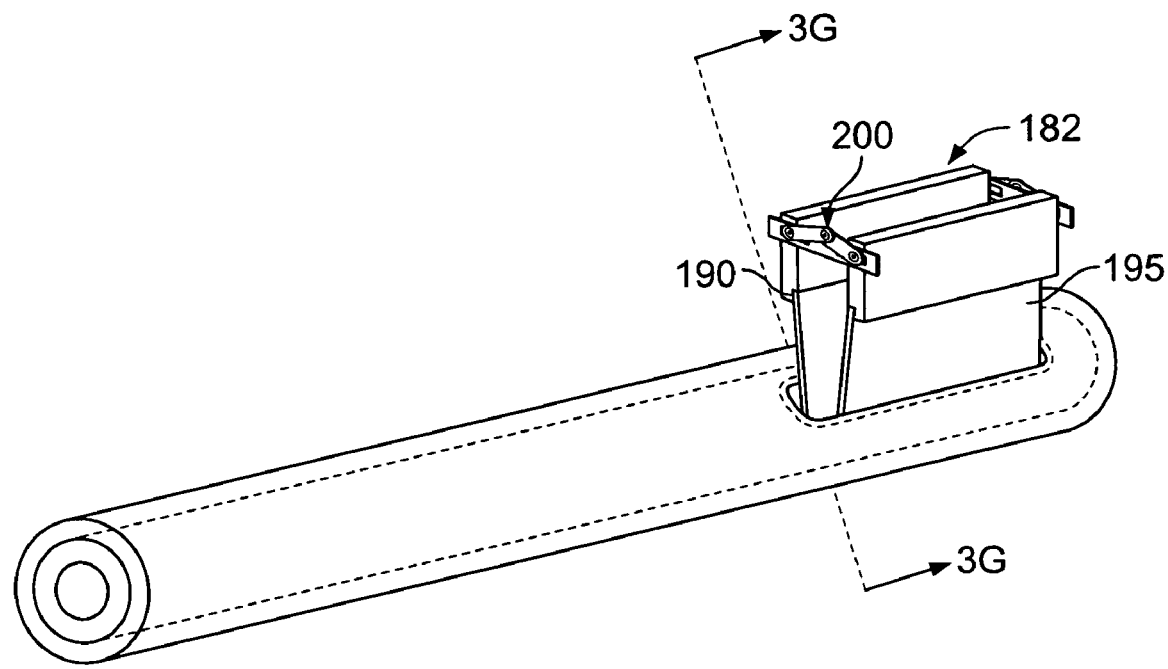
Figure 3G:
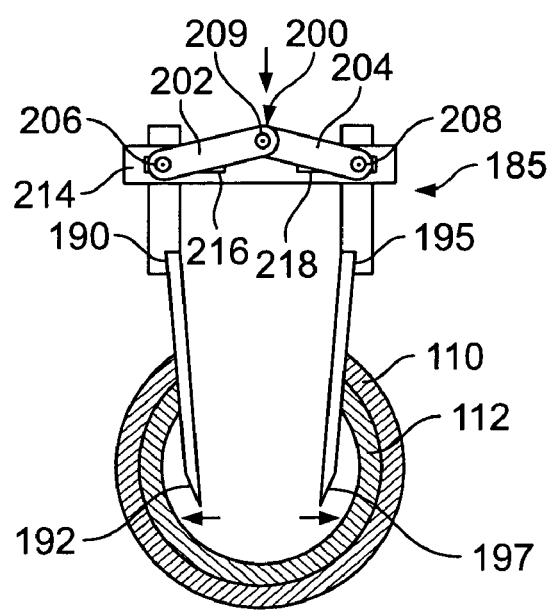

Referring to FIGS. 3E and 3C, in some embodiments, expandable member 182 includes opposed arms 190 and 195 that are operatively connected by a hinge mechanism 200. Arms 190, 195 taper to relatively narrow ends 192, 197, respectively, which can help to increase the ease with which arms 190, 195 can be inserted into slits 175, 180. Hinge mechanism 200 includes two elongate members 202, 204 that are rotatably attached to arms 190, 195 by pins 206, 208 and are rotatably connected to each other by a pin 209. As members 202, 204 are pushed downward, as shown in FIG. 3G, pins 206 and 208 slide laterally along slots 216 and 218, respectively, which are formed in a base or support member 214. As a result, arms 190, 195 also move laterally away from one another, causing slits 175, 180 to expand. Arms 190, can similarly be moved laterally toward one another by pushing upward on mechanism 202, 204 at pin 209 to allow slits 175, 180 to contract. Expandable member 182 can be manually operated and/or automated.

Other types of expandable members can alternatively or additionally be used to expand or widen slits 175, 180. Examples of other types of expandable members include pivoted plates, sliding plates, pins, and forks.

Figure 3H:
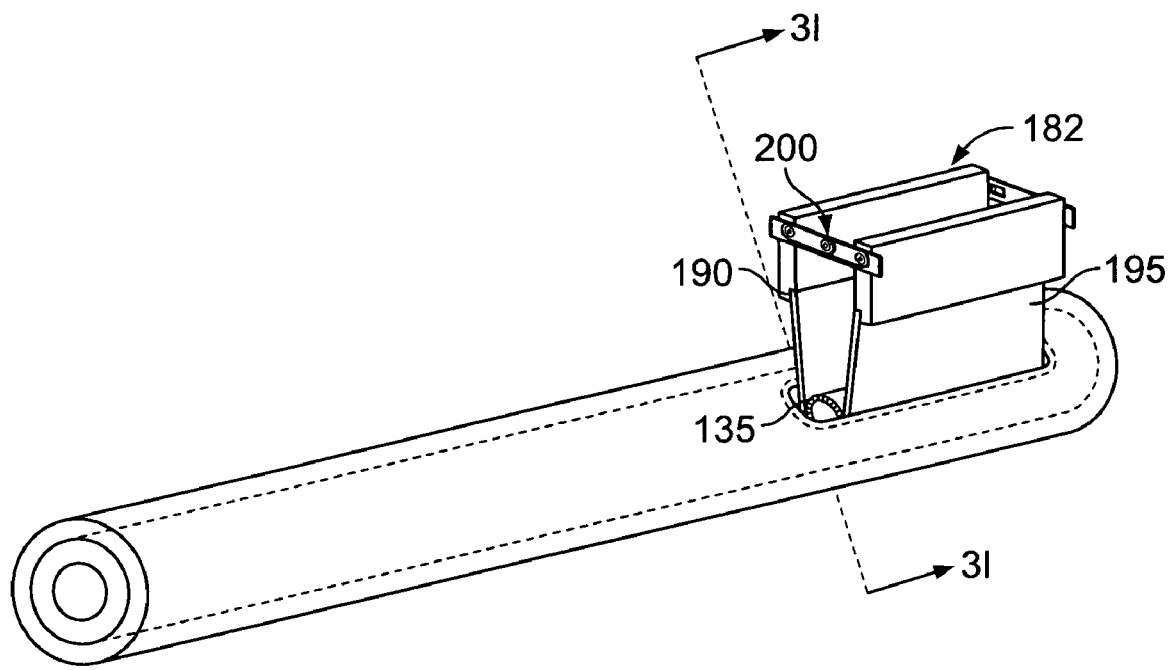
Figure 3I:
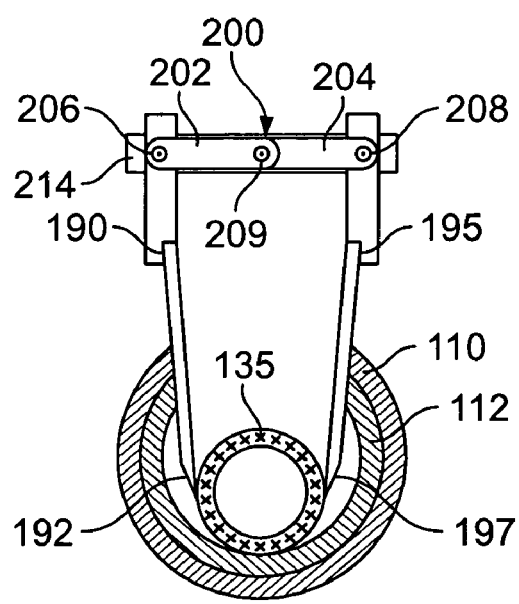

While holding slits 175, 180 in an expanded state, as shown in FIGS. 3H and 3I, stent 135 is passed through slits 175, 180 and into lumen 165 of inner sleeve 112. Stent 135 can be compressed prior to being passed through slits 175, 180. Stent 135 can, for example, be placed within a stent compression mechanism (e.g., an iris mechanism) and the stent compression mechanism can be activated to reduce the diameter of stent 135. The reduced diameter of the stent can help to enable the stent to be more easily passed through expanded slits 175, 180. In certain embodiments, stent 135 is chilled prior to or while being compressed by the stent compression mechanism. The stent can, for example, be chilled (e.g., to a temperature below a transition temperature of the material(s) from which it is formed) by a cooled fluid (e.g., cool air and/or liquid nitrogen) while compressing the stent. The temperature of the stent can, for example, be reduced to about −20° C. to about −80° C. (e.g., about −40° C.). Chilling stent 135 can help to retain the stent in its compressed configuration while it is being transferred into inner sleeve 112 via slits 175, 180.

To dispose stent 135 within lumen 165 of inner sleeve 112, stent 135 is delivered to the slit region of outer member 110 and inner sleeve 112, and then passed through slits 175, 180 and into lumen 165. Stent 135 can, for example, be delivered to the slit region of outer member 110 and inner sleeve 112 on a rod (not shown). An end portion of the rod and stent 135 can be lowered into lumen 165 via slits 175, 180, and then the rod can be removed from stent 135 (e.g., from the distal end of stent 135), leaving stent 135 within lumen 165. The proximal and/or distal ends of stent 135 can abut outer member 110 and inner sleeve 112 adjacent the proximal and/or distal ends of slits 175, 180 to prevent axial movement of stent 135 as the rod is withdrawn.

As an alternative to or in addition to using a rod to deliver stent 135 to the slit regions of outer member 110 and sleeve 112, other tools and/or techniques can be used. For example, push plates, gravity, hydraulic pressure, pneumatic pressure, a vacuum, and/or magnetic force can be used to deliver stent 135 to the slit regions of outer member 110 and sleeve 112. Any of the various mechanisms used to deliver stent 135 to the slit regions of outer member 110 and inner sleeve 112 can be manually operated and/or automated.

Other techniques can alternatively or additionally be used to dispose stent 135 in lumen 165 of inner sleeve 112. For example, arms 190, 195 can be expanded to an intermediate position (e.g., a less than fully expanded position) and stent 135 can be positioned therebetween. For example, stent 135 can be lowered or dropped into the space between arms 190, 195 from an opening formed between arms 190, 195 at the top of expandable member 182. In some embodiments, inner surfaces of arms 190, 195 are coated with a soft material to help prevent damaging the outer surface of stent 135. Examples of soft materials include polytetrafluoroethylenes (PTFEs), polyurethanes, silicones, nylons, homopolymer acetals (e.g., Delrin®), and polyvinyl chlorides (PVCs). Arms 190, 195 of expandable member 182 can then be fully expanded to allow stent 135 to drop into lumen 165 of inner sleeve 112.

After disposing stent 135 within inner sleeve 112, arms 190, 195 are removed from slits 175, 180, leaving stent 135 disposed within lumen 165 of inner sleeve 112. After arms 190, 195 have been removed from slits 175, 180, the slits contract, causing outer member 110 and inner sleeve 112 to substantially return their original dimensions.

Figure 3J:
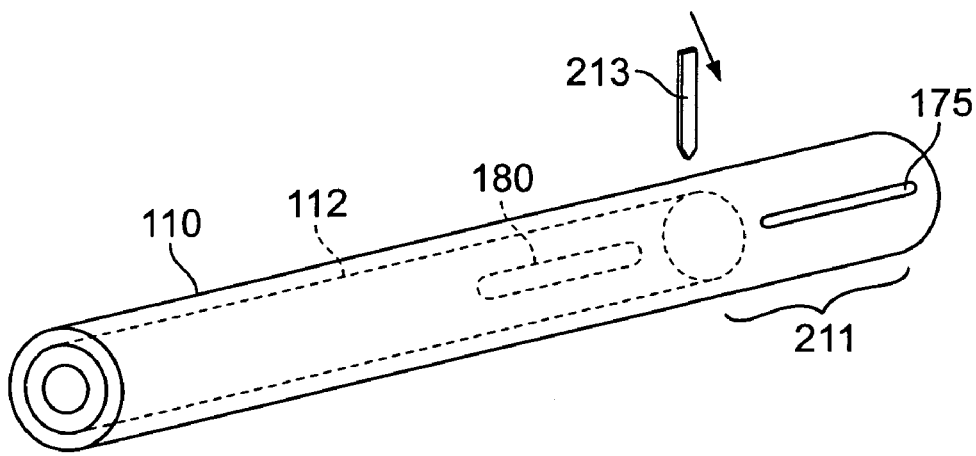

Referring to FIG. 3J, after stent 135 has been disposed within inner sleeve 112 and expandable member 182 has been removed from slits 175, 180, stent 135 and inner sleeve 112 are proximally transported to an unslit region of outer member 110. Transporting stent 135 and inner sleeve 112 can, for example, include displacing stent 135 and inner sleeve 112 proximally by a distance greater than or equal to the length of slits 175, 180, while holding outer member 110 in a substantially fixed axial position. After being displaced, the distal ends of stent 135 and/or inner sleeve 112 can, for example, be substantially adjacent the proximal ends of slits 175, 180. The unslit region can provide greater radial strength than slit region 211. Therefore, transporting inner sleeve 112 and stent 135 to the unslit region of outer member 110 can help to ensure that stent 135 remains properly constrained within outer member 110 until it is deployed within a body vessel.

Various techniques can be used to transport inner sleeve 112 and stent 135 to the unslit region of outer member 110. In certain embodiments, a pushrod is brought into contact with a distal end of inner sleeve 112 and pushed proximally while holding outer member 110 in a fixed axial position. In some embodiments, the proximal end of inner sleeve 112 is pulled proximally relative to outer member 110. In certain embodiments, a pressurized fluid source (e.g., a pressurized air source) is arranged near a distal end of outer member 110 to force fluid (e.g., air) through lumen 145 of outer member 110 in order to displace inner sleeve 112 and stent 135 relative to outer member 110.

After transporting stent 135 and inner sleeve 112 away from slit region 211 of outer member 110, slit region 211 of outer member 110 is cut off by passing a sharp blade 213 through outer member 110. Blade 213 can, for example, be passed through outer member 110 at a location proximal to slit 175 of outer member 110. As an alternative to or in addition to using blade 213 to cut off slit region 211 of outer member 110, other techniques can be used. Examples of other techniques that can be used to remove slit region 211 of outer member 110 include laser cutting, die cutting, blade cutting, grinding, and/or chemically ablating outer member 110.

Figure 3K:
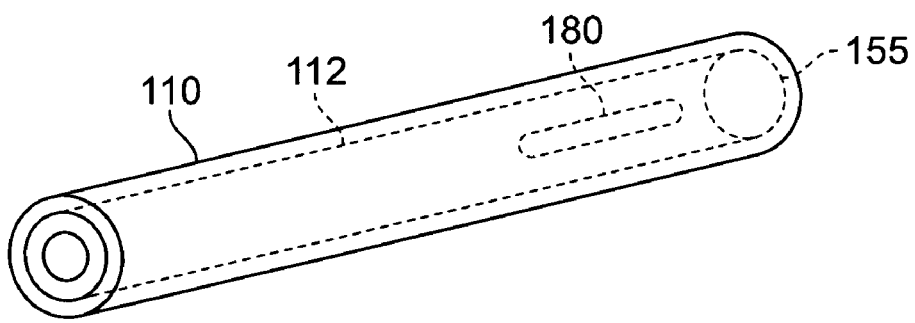

After removing slit region 211 of outer member 110, distal ends 150, 155 of outer member 110 and inner sleeve 112, respectively, can be substantially aligned with one another, as shown in FIG. 3K. Inner member 105 (FIG. 1) can then be disposed within the lumens of outer member 110, inner sleeve 112, and stent 135. Inner member 105, outer member 110, and inner sleeve 112 can be attached at their proximal ends to a handle or control device (not shown). The handle or control device can include a mechanism (e.g., a thumb wheel) that enables the user to retract outer member 110 and inner sleeve 112 relative to inner member 105.

In certain embodiments, outer member 110 includes (e.g., is formed of) one or more polymers. Examples of polymers include polyether-block co-polyamide polymers (e.g., Pebax®), copolyester elastomers (e.g., Arnitel® copolyester elastomers), thermoset polymers, polyolefins (e.g., Marlex® polyethylene, Marlex® polypropylene), high-density polyethylenes (HDPEs), low-density polyethylenes (LDPEs), polyamides (e.g., Vestamid®), polyetheretherketones (PEEKs), polyvinyl chlorides (PVCs), and silicones. Other examples of polymers include thermoplastic polymers, such as polyamides (e.g., nylon), thermoplastic polyester elastomers (e.g., Hytrel®), and thermoplastic polyurethane elastomers (e.g., Pellethane®). Outer member 110 can alternatively or additionally include one or more metals, such as stainless steel and nitinol. In some embodiments, outer member 110 includes a braided structure, such as a braided metal tube.

Inner sleeve 112 can include (e.g., can be formed of) one or more lubricious materials, such as polytetrafluoroethylene (PTFE). In certain embodiments, the inner surface and/or outer surface of inner sleeve 112 is/are coated with PTFE, Glidex®, Hydropass®, and/or other lubricious coatings. In embodiments in which inner sleeve 112 is formed of a lubricious material and/or the inner surface of inner sleeve 112 is coated with a lubricious material, the amount of friction between the inner surface of inner sleeve 112 and the outer surface of stent 135 can be reduced as compared to inner sleeves that are formed of non-lubricious materials and/or are coated with non-lubricious materials. The reduced friction between inner sleeve 112 and stent 135 can help to prevent the outer surface of stent 135 from being scratched or scuffed when inner sleeve 112 and stent 135 are moved relative to one another, e.g., when stent 135 is being loaded into inner sleeve 112 and when inner sleeve 112 is retracted to deploy stent 135. In addition, the use of a sleeve formed of and/or coated with a low-friction material can help to reduce axial compression (e.g., foreshortening) and/or axial stretching of the stent as the inner sleeve is retracted relative to the stent. In embodiments in which inner sleeve 112 is formed of a lubricious material and/or the outer surface of inner sleeve is coated with a lubricious material, the amount of friction between the outer surface of inner sleeve 112 and the inner surface of outer member 110 can also be reduced. The reduced friction can help to increase the ease with which inner sleeve 112 is retracted relative to outer member 110 and/or stent 135, such as when inner sleeve 112 and stent 135 are being transported away from the slit region of outer member 110 during the above-described stent loading process.

In some embodiments, stent 135 includes a coating. For example, stent 135 can include a drug-eluting coating. Examples of drug-eluting coatings include paclitaxel, everolimus, etc. Stent 135 can alternatively or additionally include other types of coatings, such as radiopaque coatings. Alternatively or additionally, stent 135 can include one or more uncoated surfaces.

While certain embodiments have been described above, other embodiments are possible.

As an example, while the methods described above include cutting off slit region 211 of outer member 110 after disposing stent 135 within inner sleeve 112, other techniques can alternatively or additionally be used. For example, slit region 211 can be repaired after disposing stent 135 within inner sleeve 112. After transporting stent 135 and inner sleeve 112 proximally away from the slit region of outer member 110, for example, laser energy can be applied to outer member 110 in the region of slit 175 to repair the slit (e.g., to bond together opposite surfaces that define the slit). Other bonding techniques can alternatively or additionally be used to repair slit 175 of outer member 110. Examples of bonding techniques include thermal bonding, adhesive bonding, RF bonding, laser welding, and microwave bonding. Slit 175 can alternatively or additionally be repaired using mechanical interlocking techniques. As a result of repairing slit region 211, the radial strength of outer member 110 in the slit region can be increased, which can help outer member 110 to better support stent 135 as stent 135 attempts to expand within lumen 140 and applies expansive forces to inner sleeve 112 and outer member 110. After repairing the slit region, stent 135 and inner sleeve 112 can be slid back into the repaired slit region, and stent 135 can be delivered to the targeted region of the body vessel within the repaired slit region.

Figure 4:
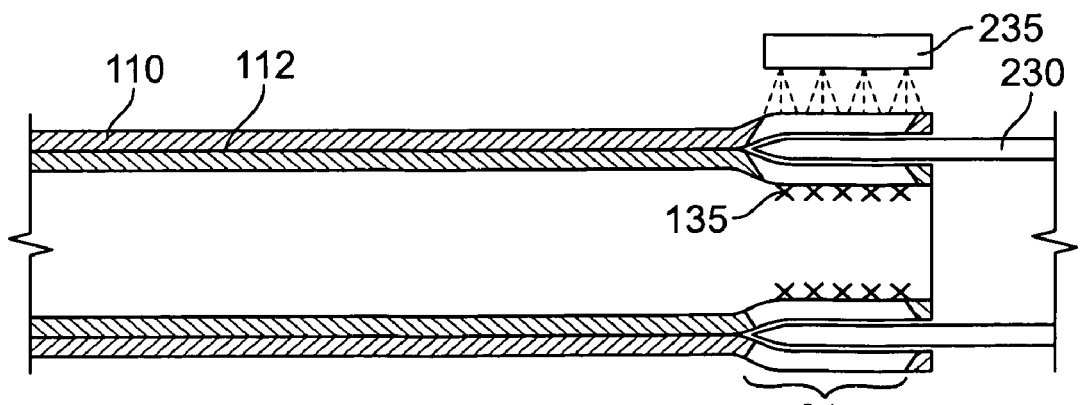
FIG. 4 is a cross-sectional view of an embodiment of a method of repairing a slit region of a tubular member during a stent loading process.

As another example, while embodiments described above include displacing stent 135 prior to repairing slit region 211 of outer member 110, slit region 211 of outer member 110 can alternatively or additionally be repaired with stent 135 positioned in the slit region (e.g., with stent 135 adjacent slit 175 of outer member 110). For example, as shown in FIG. 4, a metal tube (e.g., a steel tube) 230 can be inserted between inner sleeve 112 and outer member 110 in the slit region of inner sleeve 112 and outer member 110. Tube 230 is tapered to increase the ease with which the tube is able to be inserted between outer member 110 and inner sleeve 112. After disposing tube 230 between outer member 110 and inner sleeve 112, a laser device 235 positioned adjacent slit region 211 of outer member 110 is activated such that laser energy emitted from laser device 235 contacts and bonds together opposed surfaces that form the slits. The metal tube can help to prevent tubular member 200 from being bonded to stent 135 as slit region 211 is repaired. After repairing slit region 211, the metal tube can be removed, and outer member 110 and inner sleeve 112 can be incorporated into a stent delivery system, as described above.

Figure 5:
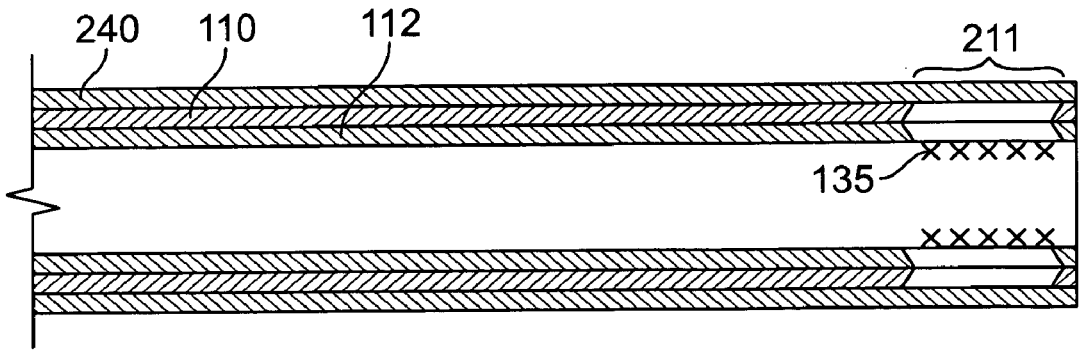
FIG. 5 is a cross-sectional view of an embodiment of a tubular member reinforced with an outer sleeve.

As a further example, as an alternative to or in addition to cutting off slit region 211 of outer member 110, an outer sleeve 240 can be disposed over the slit region of outer member 110, as shown in FIG. 5, to reinforce slit region 211. Outer sleeve 240 can extend along substantially the entire length of outer member 110. Outer sleeve can alternatively be arranged to extend about only a fraction of the length of the outer member 211 (e.g., the about slit region 211 of outer member 110). Outer sleeve 240 can include (e.g., can be formed of) one or more of the materials discussed above with respect to outer member 110. Outer sleeve 240 can have an inner diameter that is about 0.1 millimeter to about 0.8 millimeter greater than the outer diameter of outer member 110, and can have a wall thickness of about 0.1 millimeter to about one millimeter. In some embodiments, outer sleeve 240 is attached to outer member 110. For example, outer sleeve 240 (e.g., an inner surface of outer sleeve 240) can be bonded (e.g., laser bonded, thermally bonded, adhesively bonded, laser welded) to outer member 110 (e.g., an outer surface of outer member 110). Alternatively or additionally, outer sleeve 240 can be mechanically interlocked with outer member 110.

As another example, in some embodiments, inner sleeve 112 is rotated (e.g., rotated about 180 degrees) after disposing stent 135 within inner sleeve 112. As a result, the slit region of inner sleeve 112 is supported by an unslit region of outer member 110, and less pressure is exerted on the slit region of outer member 110. After rotating inner sleeve 112, the slit within outer member 110 can remain unrepaired. Alternatively, the slit within outer member 110 can be repaired after rotating inner sleeve 112 to increase the strength of outer member 110.

Figure 6:
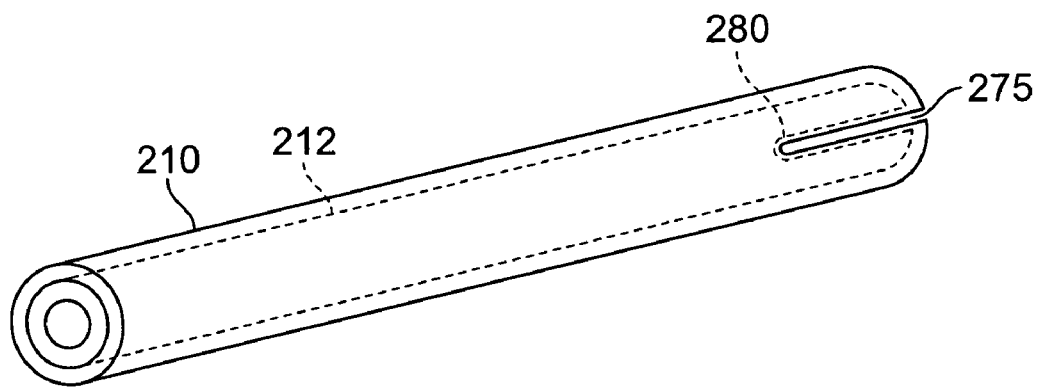
FIG. 6 is a perspective view of an embodiment of an inner sleeve including a slit extending to its distal end and an outer tubular member including a slit extending to its distal end.

As an additional example, while the slits of outer member 110 and inner sleeve 112 have been described as terminating in regions proximal to the distal ends of outer member 110 and inner sleeve 112, the slits can alternatively or additionally be arranged to extend to the ends (e.g., distal ends) of the outer member and inner sleeve. As shown in FIG. 6, for example, an outer member 210 and an inner sleeve 212 include slits 275, 280 that extend to distal ends 250, 255 of outer member 210 and inner sleeve 212, respectively. Because slits 275, 280 (as compared to slits 175, 180 of embodiments described above) are less restricted from expanding at their distal ends, this arrangement can help to increase the ease with which the slits can be expanded and can help to allow for the insertion of larger stents into outer member 210 and inner sleeve 212. In certain embodiments, multiple, circumferentially spaced slits extend to the ends (e.g., the distal ends) of the outer member and inner sleeve. In such embodiments, in addition to helping the slits to receive larger stents, this arrangement of the slits can allow the slit region of the inner sleeve to expand along with the stent during deployment of the stent. Thus, this arrangement can help to provide added control of the rate of expansion of the stent during the stent deployment process.

Figure 7:
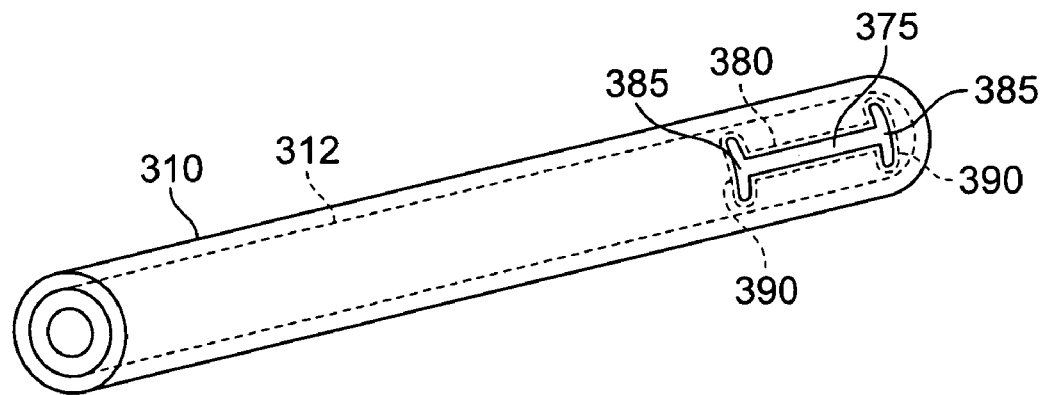
FIG. 7 is a perspective view of an embodiment of an inner sleeve and an outer tubular member including longitudinal slits and circumferential slits extending from end regions of the longitudinal slits.
Figure 8:
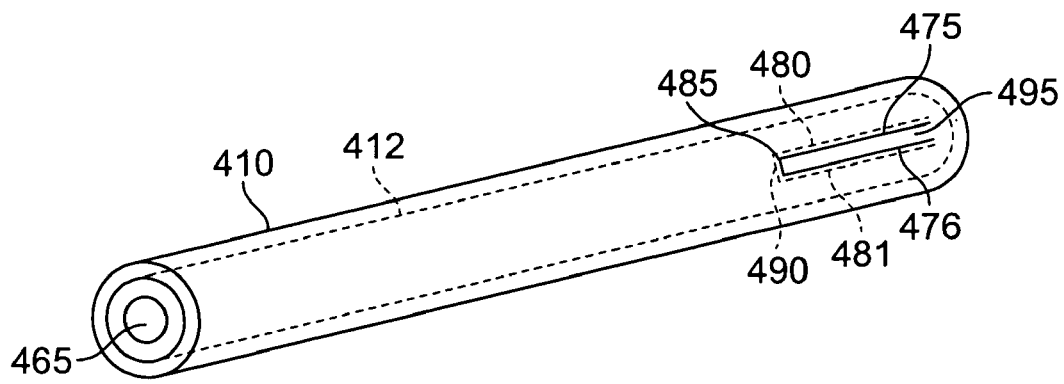
FIG. 8 is a perspective view of an embodiment of an inner sleeve and an outer tubular member including an aperture with a peelable panel disposed therein.

As a further example, while the outer members and inner sleeves of the embodiments described above include individual, longitudinal slits, the outer member and/or inner sleeve can alternatively or additionally include one or more apertures of another shape. Referring to FIG. 7, for example, an outer member 310 and an inner sleeve 312 include longitudinal slits 375, 380 and end slits 385, 390 extending substantially circumferentially about a portion of outer member 310 and inner sleeve 312 at the proximal and distal ends of longitudinal slits 375, 380. As another example, as shown in FIG. 8, an outer member 410 includes longitudinally extending slits 475, 476 and an inner sleeve 412 includes longitudinal slits 480, 481, which are substantially aligned with slits 475, 476 of outer member 410. Longitudinal slits 475, 476 and longitudinal slits 480, 481 are connected by circumferentially extending slits 485 and 490, respectively, at the proximal ends of slits 475, 476 and slits 480, 481 to form a peelable panel 495. Circumferentially extending slits 485, 490 can alternatively or additionally connect axially extending slits 485, 490 at their distal ends. Panel 495 can be peeled back to expose a substantially rectangular aperture through which stent 135 can be inserted into a central lumen 465 of inner sleeve 412. The apertures illustrated in FIGS. 7 and 8 can generally be opened wider than longitudinal slits 175, 180 described above, and can help to enable larger stents to be passed therethrough. Any of the various material removal techniques described above can be used to form these apertures.

As another example, while the stent delivery systems of the embodiments described above include an inner sleeve disposed between a stent and an outer member, in certain embodiments, the stent can be disposed directly adjacent the outer member without an inner sleeve disposed therebetween. In such embodiments, the stent can be disposed within the lumen of the outer member by passing the stent through an aperture in the outer member using one or more of the techniques described herein. After disposing the stent within the lumen of the outer member, the stent can be transported away from the region of the outer member that includes the apertures (e.g., by contacting the distal end of the stent with a pushrod and pushing the stent proximally through the lumen of the outer member) and/or the region of the outer member that includes the aperture can be cut off, repaired, and/or reinforced using one or more of the techniques described herein.

Figure 9A:
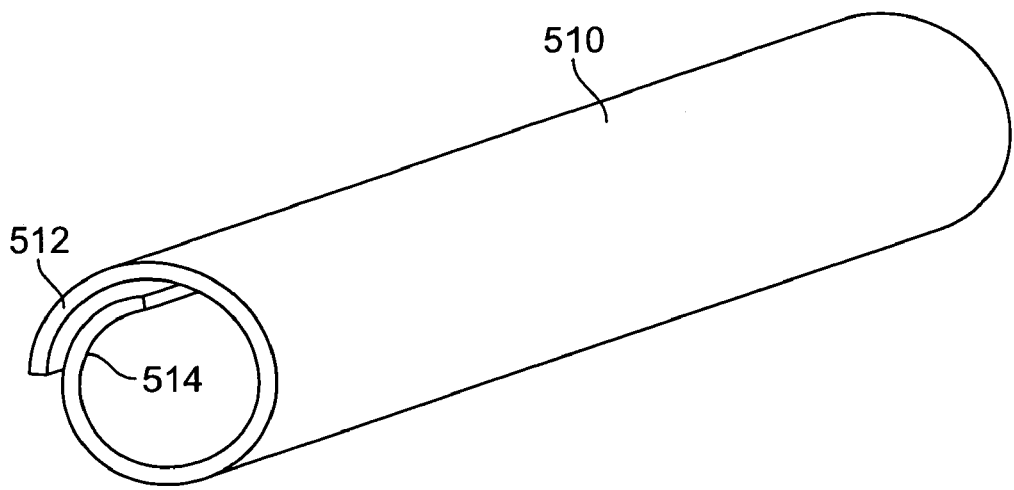
FIGS. 9A and 9B are perspective views of a coil-shaped outer tubular member in a closed and open configuration, respectively.
Figure 9B:
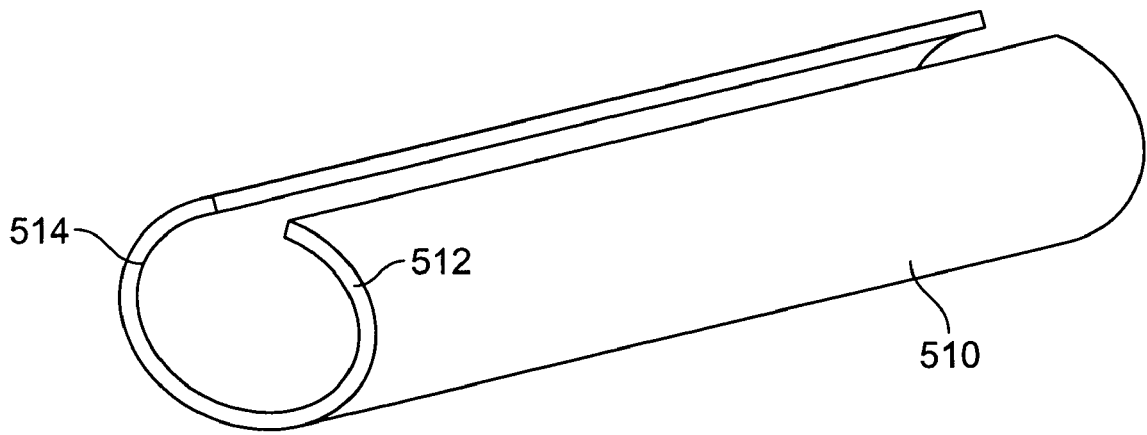

As an additional example, while the outer members of embodiments above have been described as cylindrical tubular members, the outer members can alternatively or additionally have other cross-sectional shapes. As shown in FIG. 9A, for example, a coil-shaped outer member 510 includes overlapping end regions 512 and 514. Overlapped regions 512 and 514 can be grasped and coil-shaped outer member 510 can be partially unraveled, as shown in FIG. 9B, to disposed a stent therein. The stent can, for example, be passed between regions 512 and 514 while outer member 510 is held in the partially unraveled configuration. Outer member 510 can be formed of one or more metals, such as nitinol, stainless steel, cobalt chromium, and tantalum. In some embodiments, the coil-shaped outer member has a sufficient spring force to retain the stent in a compressed state therein. The coil can, for example, have a spring force of about 0.1 kilogram to about one kilogram. In embodiments in which the coil-shaped outer member has a sufficient spring force to prevent radial expansion of the sent positioned therein, the outer member can be used without removing, repairing, and/or reinforcing the portion of the outer member through which the stent is inserted. In such embodiments, for example, the expansive forces of the stent would be unable to open the coil-shaped outer member 510 to an extent such that regions 512 and 514 would not overlap.

As a further example, in certain embodiments, the stent is compressed in a manner to change the cross-sectional shape of the stent. The stent, after being compressed, can, for example, have an oval cross-section. In such embodiments, the stent can be inserted through the slit(s) of the outer member and/or the inner sleeve with its smaller radial dimension (e.g., its width) extending about the width(s) of the slit(s). Compressing the stent in this manner can help to allow larger stents to be passed through the slits.

As an additional example, in some embodiments, the blade used to form slits in the outer member and/or inner sleeve is inserted into the outer member and/or inner sleeve at an angle (e.g., an acute angle) relative to the outer surface of the outer member and/or inner sleeve in the region of the slits. As a result, those surfaces defining the slits can be angled, which can increase the surface area of those surfaces, and thus increase the strength of the bond between those surfaces after the slits are repaired.

Figure 10A:
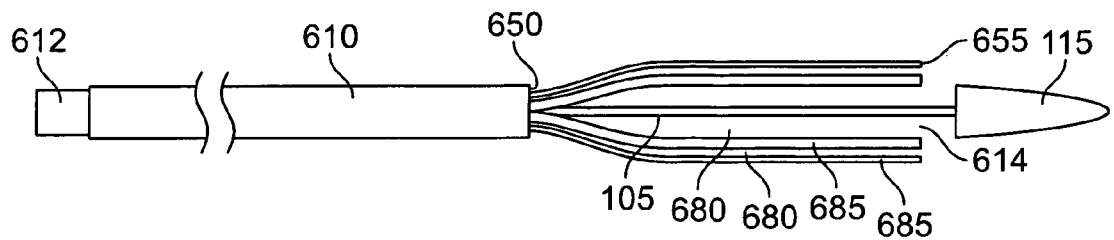
FIGS. 10A-10E illustrate an embodiment of a method and apparatus for loading a stent into an inner sleeve and an outer tubular member.

As another example, while embodiments discussed above relate to methods of loading stents that include passing the stents through apertures in side walls of tubular members, stents can alternatively or additionally be passed through apertures formed in other regions of the tubular member. Stents can, for example, be passed through the proximal and/or distal ends of the lumen extending axially through the tubular member. FIGS. 10A-10E, for example, illustrate an embodiment of a method of loading a stent into an outer tubular member via the distal end of an lumen extending axially therethrough. Referring to FIG. 10A, an inner sleeve 612 is disposed within an outer member 610, and extends distally beyond a distal end 650 of outer member 610. The portion of inner sleeve 612 extending beyond distal end 650 of outer member 610 includes multiple, circumferentially spaced slits 680 extending to a distal end 655 of inner sleeve 612 and forming tails 685 therebetween. Inner sleeve 612 can have a wall thickness of about 0.0007 inch to about 0.001 inch (about 0.0178 millimeter to about 0.025 millimeter) and can include one or more of the materials described herein with respect to the inner sleeves described above. Inner member 105 is disposed within and extends axially through outer member 610 and inner sleeve 612.

Figure 10B:
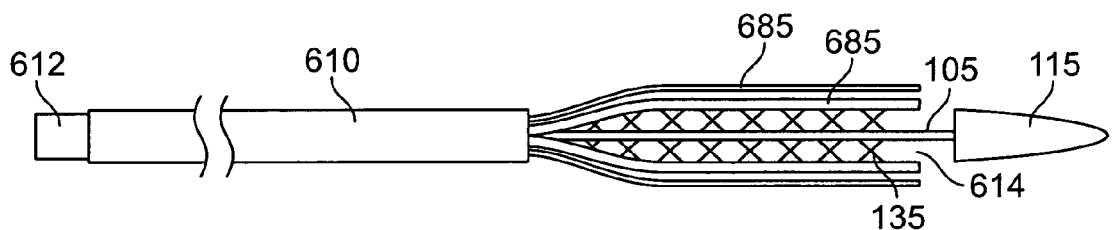

As shown in FIG. 10B, stent 135 can be disposed within the slit region of inner sleeve 612 such that tails 685 surround stent 135. Stent 135 can, for example, be disposed within the slit region of inner sleeve 612 by passing stent 135, in an uncompressed state, over distal end 115 of inner member 105 and through a distal end 614 of a lumen extending axially through inner sleeve 612.

Figure 10C:
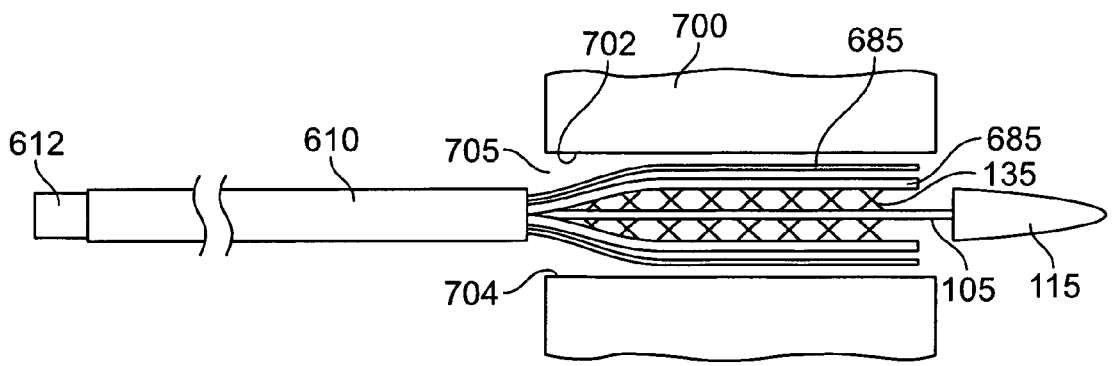
Figure 10D:
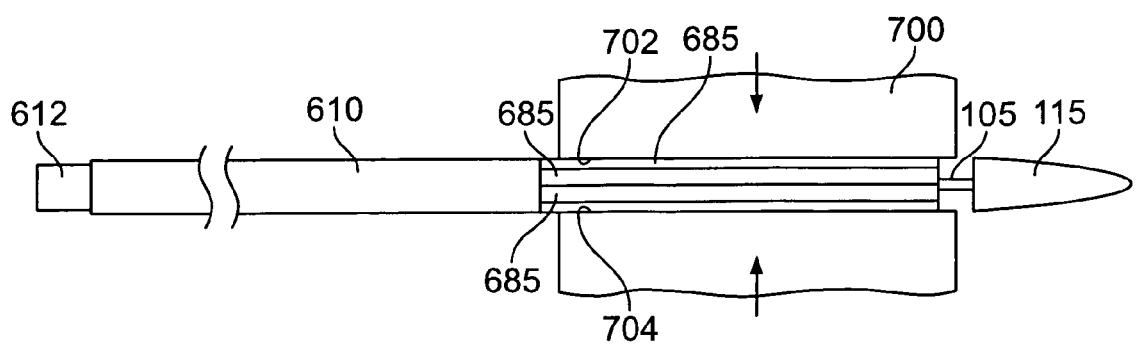

Referring to FIG. 10C, after disposing stent 135 within the slit region of inner sleeve 612, the stent-carrying portion of inner member 105 (e.g., the portion of inner member 105 surrounded by stent 135), stent 135, and the slit region of inner sleeve 612 are disposed within a recess 705 formed by a stent compressing mechanism (e.g., an iris mechanism) 700. Stent compressing mechanism 700 is then activated, as shown in FIG. 10D, causing opposed surfaces 702, 704 to compress (e.g., to reduce the diameter of) stent 135. Tails 685 of inner sleeve 612 can help to prevent the outer surface (e.g., the coated outer surface) of stent 135 from being scratched or scuffed by stent compressing mechanism 700. Distal tip 115 of inner member 105, which has a larger outer diameter than the stent-carrying portion of inner member 105, extends beyond a distal end 710 of stent compressing mechanism 700. This arrangement can help to prevent distal tip 115 from hindering the compression of stent 135 by, for example, preventing recess 705 of stent compressing mechanism 700 from reaching its fully reduced diameter. Alternatively or additionally, stent compressing mechanism 700 can include a recess or chamber for receiving distal tip 115 as stent compressing mechanism 700 is activated. The recess or chamber can, for example, have an inner diameter in the fully reduced position that is greater than or equal to the outer diameter of distal tip 115. In some embodiments, stent 135, in addition to being compressed, is cooled using any of the various cooling techniques described herein. As discussed above, reducing the temperature of stent 135 can help to retard the expansion of stent 135.

Figure 10E:
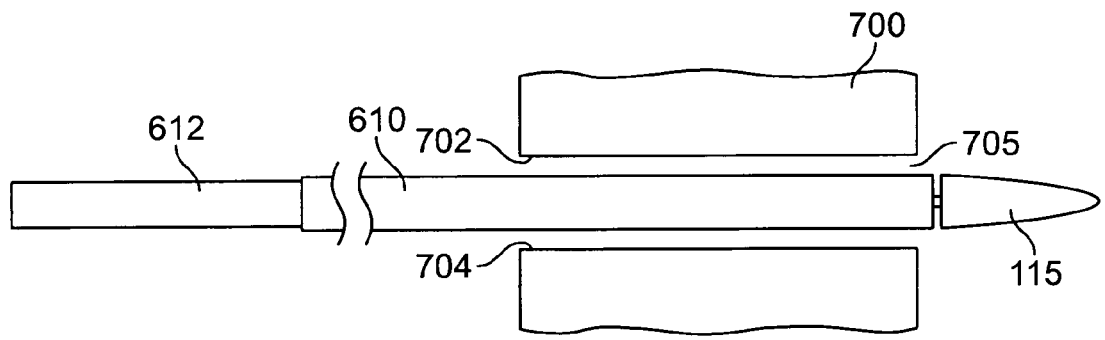

As shown in FIG. 10E, after compressing stent 135 about inner member 105, stent compression mechanism 700 is deactivated, allowing recess 705 to return to its original, unreduced size and shape. Upon deactivating stent compression mechanism 700, stent 135 remains in a substantially compressed configuration. The compressed stent can, for example, have an outer diameter that is about one millimeter to about five millimeters less than the inner diameter of outer member 610. Outer member 610 is then advanced distally relative to inner sleeve 612 and inner member 105 so that stent 135 and tails 680 become disposed within a central lumen of outer member 610, as shown in FIG. 10E. Tails 685 of inner sleeve 612, by surrounding stent 135 as outer member 610 is moved over stent 135, can help to prevent the outer surface of stent 135 from being scratched or scuffed by the distal end surface and/or inner surface of outer member 610. Outer member 610, after being advanced distally relative to inner sleeve 612 and stent 135, covers substantially the entire length of stent 135 and can help to prevent premature expansion of stent 135. Inner member 105, outer member 610, inner sleeve 612, and stent 135 can then be removed from stent compression mechanism 700.

A control member or handle (not shown) can be attached to proximal portions of inner member 105, outer member 610, and inner sleeve 612 to form a stent delivery system 600 (FIGS. 11A-11E). The control member can be attached to inner member 105, outer member 610, and inner sleeve 612 prior to or subsequent to inserting those components into stent compression mechanism 700. The control member can include one or more mechanisms (e.g., thumb wheels, pull grips, etc.) to allow a user to retract outer member 610 and/or inner sleeve 612 relative to inner member 105 and stent 135. In some embodiments, one or more portions of inner sleeve 612 and outer member 610 are detached from one another, allowing outer member 610 to be retracted proximally relative to inner sleeve 612.

Figure 11A:
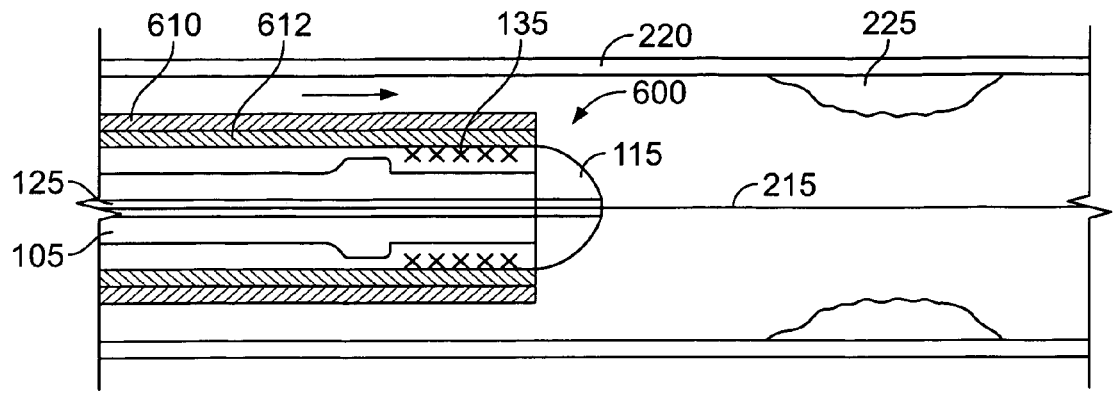
FIGS. 11A-11D illustrate an embodiment of a method of using a stent delivery system.
Figure 11B:
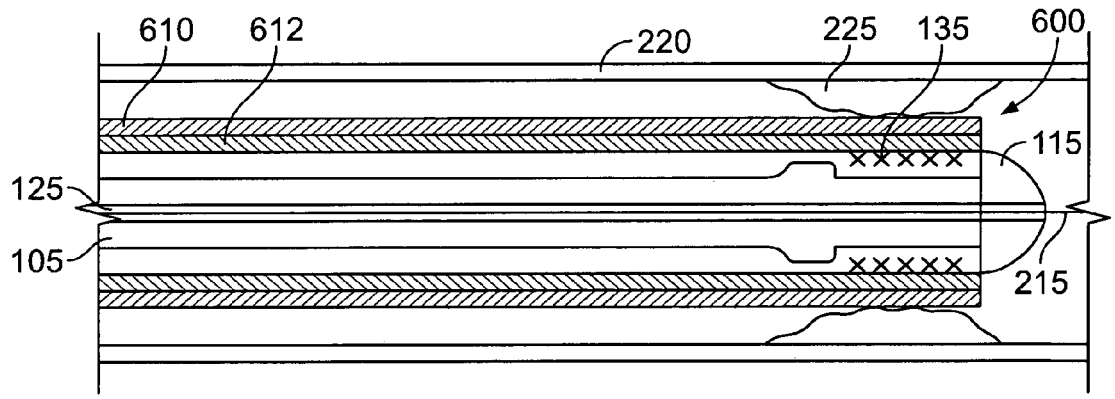
Figure 11C:
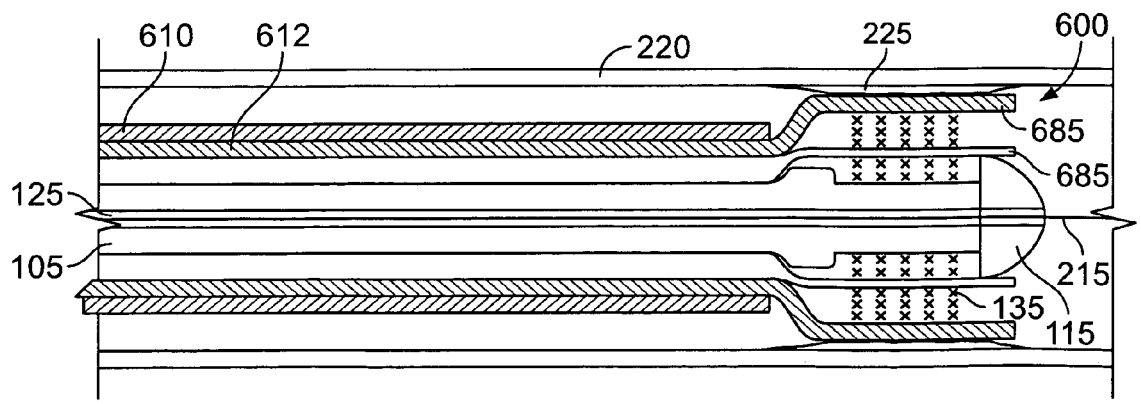
Figure 11D:
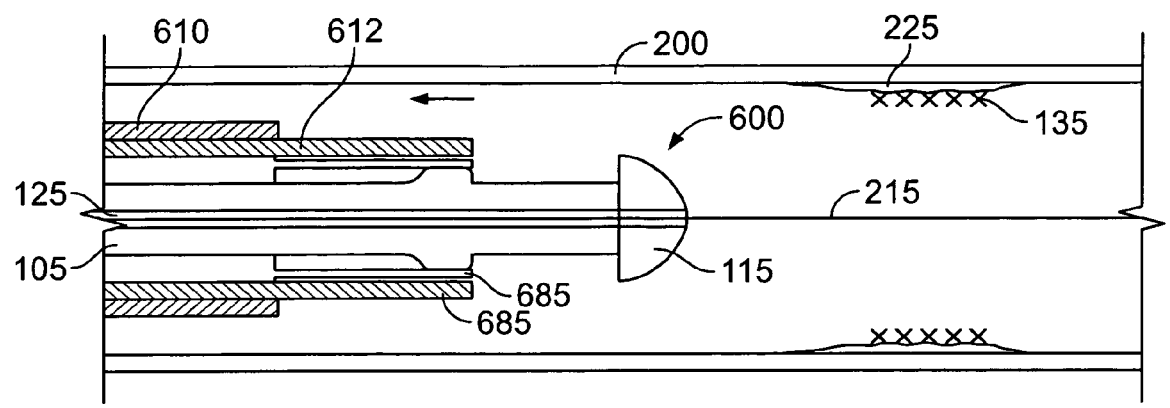

FIGS. 11A-11D illustrate an embodiment of a method of using stent delivery system 600. Referring to FIG. 11A, the method includes inserting guide wire 215 into body vessel 220 and then feeding stent delivery system 600 over guide wire 215 so that guide wire 215 becomes disposed within guide wire lumen 125 extending through inner member 105. Stent delivery system 600 is then advanced along guide wire 215 and through body vessel 220 until the portion of stent delivery system 600 in which stent 135 is contained (e.g., the slit region of inner sleeve 612 including tails 685) is positioned within occluded region 225 of vessel 220, as shown in FIG. 11B. Referring to FIG. 11C, after stent delivery system 600 is positioned within occluded region 225 of vessel 220, outer member 610 is retracted, allowing stent 135 to expand. The expansion of stent 135 causes tails 685 of inner sleeve 612 to become positioned (e.g., to become compressed) between stent 135 and vessel 220. As shown in FIG. 11D, tails 685 are then removed from between stent 135 and the vessel wall by applying a proximal force to a proximal portion of inner sleeve 612. After tails 685 have been removed from between stent 135 and the vessel wall, stent delivery system 600 is withdrawn from body vessel 220, leaving stent 135 implanted within the vessel.

Figure 12:
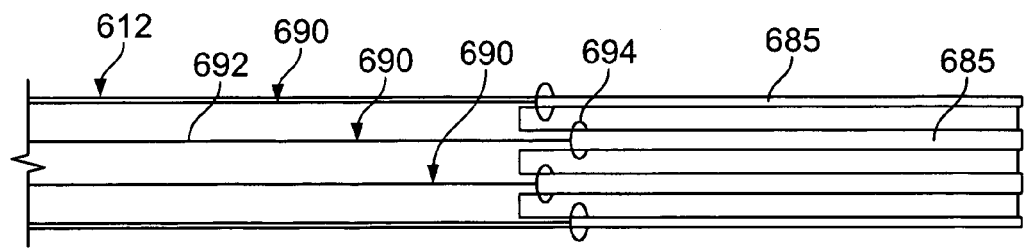
FIG. 12 is a side view of an inner sleeve including multiple circumferentially spaced tails in its distal end region with a retraction mechanism secured to each of the tails.

While tails 685 have been described as being removed from between stent 135 and vessel 220 by pulling proximally on a proximal portion of inner sleeve 612, in some embodiments, each tail includes an individual retraction mechanism. Referring to FIG. 12, for example, a looped wire 690 is disposed around each of tails 685. Looped wire 690 includes an elongate wire 692 and a loop member 694 secured to the distal end of wire 692. The looped wire can alternatively be formed of a single elongate member looped at its distal end. Pulling proximally on looped wire 690 causes tail 685, about which loop 694 is disposed, to be retracted. By providing each of the tails with a looped wire, the tails can be individually removed from their position between the stent and the vessel wall. Individually removing tails 685 can help to reduce the amount of friction experienced between tails 685 and stent 135 as the tails are retracted. Thus, this arrangement can help to maintain the axial position of the stent within the vessel and can help to reduce scratching or scuffing of the outer surface of the stent.

Stent delivery system 600 can alternatively or additionally be used to deliver and deploy stent 135 in a manner similar to that described above with respect to stent delivery system 100. For example, outer member 610 and inner sleeve 612 can be retracted at substantially the same time to allow stent 135 to be deployed within the vessel without trapping tails 685 of inner sleeve 612 against the vessel wall. In some embodiments, outer member 610 (e.g., the inner surface of outer member 610) and inner sleeve 612 (e.g., the outer surface of inner sleeve 612) are attached to one another along at least a portion of their lengths to allow outer member 610 and inner sleeve 612 to be retracted using a common retraction mechanism.

Figure 13:
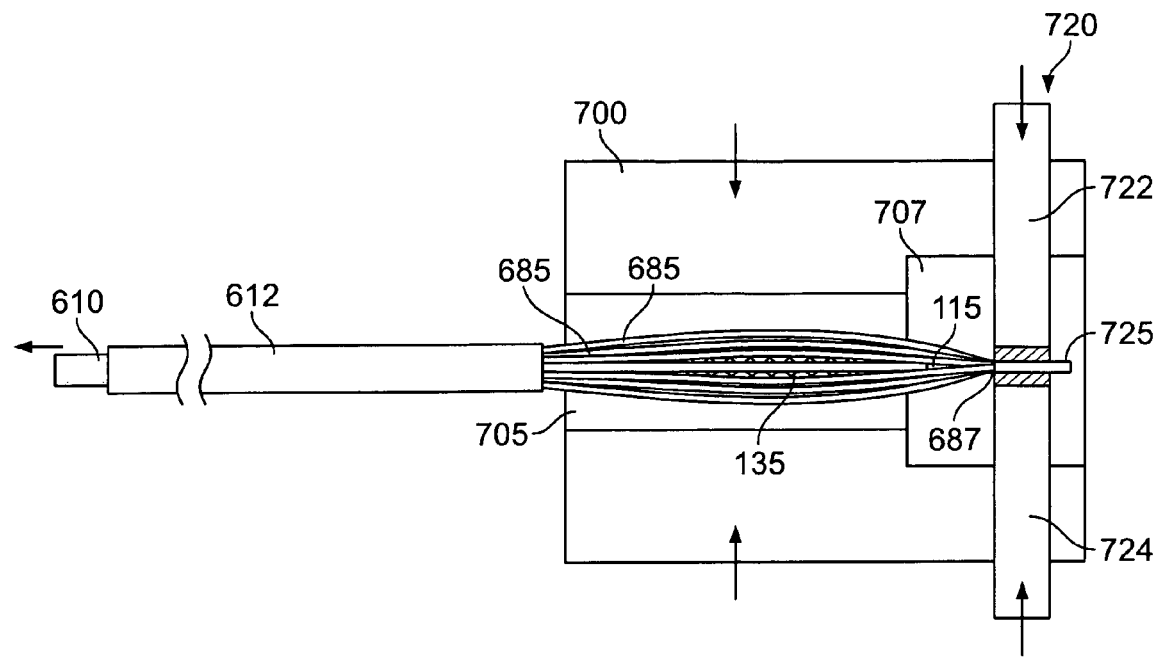
FIG. 13 illustrates an embodiment of a method of loading a stent into an outer tubular member while restraining distal ends of elongate tails that surround the stent.

Referring to FIG. 13, in certain embodiments, tails 685 are arranged to extend distally beyond the distal ends of stent 135 and inner member 105. Distal regions 687 of tails 685 are disposed within a recess 725 formed between opposed members 722 and 724 of a clamping mechanism 720. Clamping mechanism 720 is then activated, as shown in FIG. 13, to axially restrain distal regions 687 of tails 685 between opposed member 722 and 724, and a proximal force is applied to inner sleeve 612 to produce tension in tails 685. The tension in tails 685 can help to compress stent 135 and can help tails 685 to maintain a desired circumferential orientation (e.g., helps to prevent adjacent tails from overlapping one another in the region of the stent). While applying slight tension to tails 685, stent compressing mechanism 700 can be activated to compress stent 135, thereby reducing the diameter of stent 135. As shown in FIG. 13, in addition to recess 705, stent compressing mechanism 700 includes a recess or chamber 707 configured to receive distal end 115 of inner member 105 when stent compressing mechanism 700 is compressed. Recess 707 can, for example, have a larger inner diameter than recess 705 when stent compressing mechanism 700 is activated or reduced. This can help to prevent distal end 115 of inner member 105 from adversely affecting the compression of stent 135. After compressing stent 135, stent compressing mechanism 700 and clamping mechanism 720 are deactivated, and outer member 110 is advanced distally relative to inner sleeve 612 and stent 135 to capture tails 685 and stent 135 therein. Subsequently, tails 685 can be removed from (e.g., cut off of) inner sleeve 612.

Figure 14:
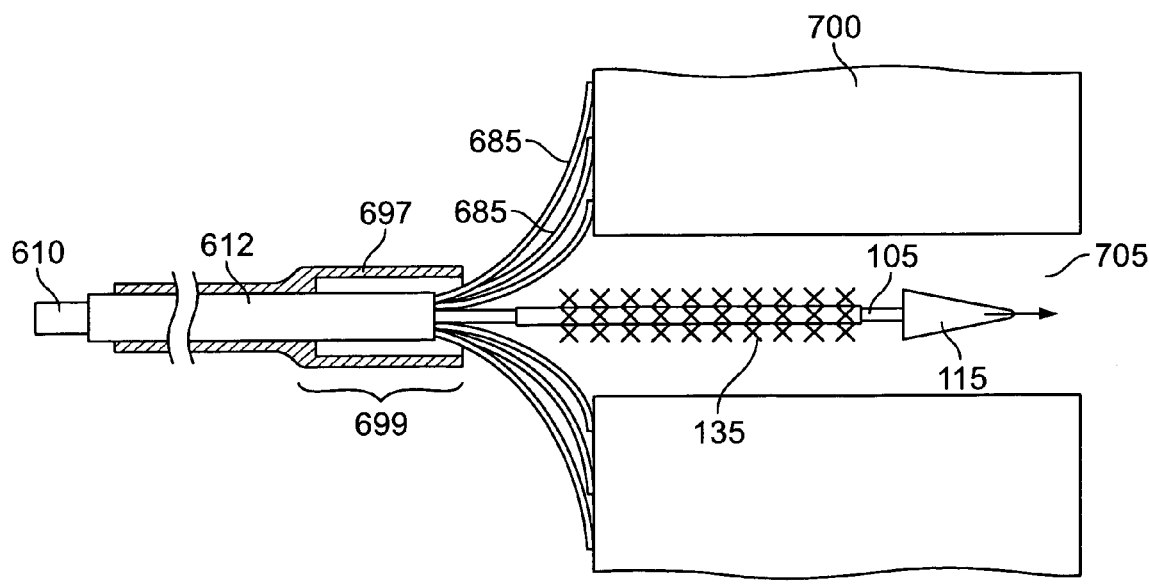
FIG. 14 illustrates an embodiment of a method of loading a stent into an outer tubular member.

While embodiments have been described in which stent 135 is crimped while tails 685 surround the stent, the stent can alternatively or additionally be inserted into the stent compression mechanism and crimped without tails 685 surrounding the stent. As shown in FIG. 14, for example, tails 685 are splayed radially outward at a proximal end of stent compressing mechanism 700 while inserting stent 135 into recess 705 of stent compression mechanism 700. After positioning stent 135, as desired, within stent compressing mechanism 700, the stent compressing mechanism is activated to reduce the diameter of stent 135 around inner member 105. After compressing stent 135, outer member 610 can be displaced distally relative to inner sleeve 612 and stent 135, as discussed above. A guide tube 697 is secured around the distal portion of outer member 610. A distal region 699 of guide tube 697 has an inner diameter that is larger than the outer diameter of outer member 610. Thus, as outer member 610 and guide tube 697 are advanced distally over inner sleeve 612, guide tube 697 can help to guide tails 685 into the central lumen of outer member 610. This arrangement can help to maintain a desired circumferential orientation of tails 685 around stent 135. Guide tube 697 can, for example, help to prevent tails 685 from overlapping one another as outer member 610 is advanced distally and receives tails 685 and stent 135 therein. In certain embodiments, guide tube 697 is releasably secured to outer member 610 such that after tails 685 are disposed in outer member 610, guide tube 697 can be removed. In such embodiments, after advancing outer member 610 and guide tube 697 distally and prior to inserting system 600 into a body vessel, guide tube 697 can be removed to reduce the profile of the stent delivery system.

As another example, while the outer members and inner sleeves in embodiments above have been described as having substantially circular cross-sections, the outer member and inner sleeve can alternatively or additionally have other cross-sections, such as octagonal cross-sections, hexagonal cross-sections, pentagonal cross-sections, rectangular cross-sections, and triangular cross-sections.

As an additional example, in certain embodiments, a support member (e.g., a braid or a series of rings) extends along the outer member, outer sleeve, and/or inner sleeve. The support member can, for example, be formed of a metal, such as stainless steel. The support member can help to increase the radial strength the outer member, outer sleeve, and/or inner sleeve.

As a further example, while the methods described above include the step of deploying stent 135 within an occluded region of a body vessel, stent 135 can alternatively or additionally be deployed within other regions of a body vessel. For example, stent 135 can be delivered to and deployed within a weakened region of a body vessel.

As another example, while the methods and devices described above include self-expanding stents, other types of endoprostheses can alternatively or additionally be used. Examples of other types of endoprostheses include expandable stents (e.g., balloon-expandable stents), grafts, and stent-grafts.

Other embodiments are within the scope of the following claims.

What is claimed is:

1. A method, comprising:
   providing an implantable medical endoprosthesis;
   providing an elongate member having a sidewall, an outer surface, and a lumen; and
   moving the implantable medical endoprosthesis from a position along the outer surface of the elongate member, through an aperture formed through the sidewall of the elongate member, and into the lumen of the elongate member;
   wherein the elongate member of the medical device comprimises an outer sheath of a stent delivery system, and the implantable medical endoprosthesis comprises a stent.

2. The method of claim 1, wherein the aperture is a slit.

3. The method of claim 2, wherein the slit extends to a distal end of the elongate member.

4. The method of claim 1, wherein the aperture has a length that is greater than alength of the implantable medical endoprsthesis.

5. The method of claim 1, further comprising forming the aperture in the sidewall of the elomgate member.

6. The method of claim 1, further comprising expanding the aperture prior to passing the implantable medical endoprosthesis therethrough.

7. The method of claim 1, further comprising passing the implantable medical endoprosthesis through an aperture formed through a sidewall of an inner sleeve disposed within a lumen of the elongate member.

8. The method of claim 7, further comprising axially displacing the inner sleeve and the implantable medical endoprosthesis disposed therin relative to the aperture of the elongate member.

9. The method of claim 1, further comprising the seperating a region of the elongate member comprising the aperture from a remainder of the member.

10. The method of claim 1, further comprising disposing an outer sleeve coaxially about the elongate member, the outer sleeve substantially covering the aperture.

11. The method of claim 1, further comprising closing the aperture.

12. The method of claim 1, further comprising passing the stent through an aperture formed through a sidewall of an inner sleeve disposed within a lumen of the outer sheath.

* * * * *

UNITED STATES PATENT AND TRADEMARK OFFICE
CERTIFICATE OF CORRECTION

| | | |
|---|---|---|
| PATENT NO. | : 7,815,670 B2 | Page 1 of 1 |
| APPLICATION NO. | : 11/484528 | |
| DATED | : October 19, 2010 | |
| INVENTOR(S) | : Michael Austin et al. | |

It is certified that error appears in the above-identified patent and that said Letters Patent is hereby corrected as shown below:

Column 14
Line 61 delete "comprimises", and insert therefor -- comprises --.

Column 15
Line 3 delete "endoprsthesis", and insert therefor -- endoprothesis --.
Line 5 delete "elomgate", and insert therefor -- elongate --.
Line 15 delete "therin", and insert therefor -- therein --.

Column 16
Line 1 delete "the seperating", and insert therefor -- separating --.

Signed and Sealed this
Fourth Day of January, 2011

David J. Kappos
*Director of the United States Patent and Trademark Office*